(12) United States Patent
Onkawa et al.

(10) Patent No.: US 8,992,752 B2
(45) Date of Patent: Mar. 31, 2015

(54) GAS SENSOR ELEMENT AND GAS SENSOR

(75) Inventors: Masaki Onkawa, Konan (JP); Shigehiro Otsuka, Gifu (JP); Seiji Oya, Aichi (JP); Satoshi Teramoto, Nisshin (JP); Kuniharu Tanaka, Komaki (JP); Takeshi Mitsuoka, Konan (JP)

(73) Assignee: NGK Spark Plug Co., Ltd., Aichi-ken (JP)

( * ) Notice: Subject to any disclaimer, the term of this patent is extended or adjusted under 35 U.S.C. 154(b) by 525 days.

(21) Appl. No.: 13/401,221

(22) Filed: Feb. 21, 2012

(65) Prior Publication Data

US 2012/0211362 A1 Aug. 23, 2012

(30) Foreign Application Priority Data

Feb. 22, 2011 (JP) .................................. 2011-035583
Dec. 19, 2011 (JP) .................................. 2011-276929

(51) Int. Cl.
*G01N 27/407* (2006.01)

(52) U.S. Cl.
CPC .................................. *G01N 27/4077* (2013.01)
USPC ........................................ 204/429; 204/431

(58) Field of Classification Search
CPC .......... G01N 27/4071; G01N 27/4072; G01N 27/409
See application file for complete search history.

(56) References Cited

U.S. PATENT DOCUMENTS

| | | | |
|---|---|---|---|
| 5,419,828 A * | 5/1995 | Nakano et al. ................. | 204/425 |
| 2007/0170057 A1 | 7/2007 | Kobayashi et al. | |
| 2010/0006433 A1 | 1/2010 | Yasuda et al. | |

FOREIGN PATENT DOCUMENTS

| | | | |
|---|---|---|---|
| CN | 1329247 A | 1/2002 | |
| CN | 1441245 A | 9/2003 | |
| CN | 1707255 A | 12/2005 | |
| DE | 102006003996 A1 * | 2/2008 | .......... G01N 27/407 |
| JP | 2003-322632 A | 11/2003 | |

OTHER PUBLICATIONS

EPO machine-generated English language translation of Braun et al. DE 102006039964 A1, patent published Feb. 28, 2008.*
JPO machine-generated English language translation of JP 2003-322632 A, patent published Nov. 14, 2003.*

(Continued)

*Primary Examiner* — Alex Noguerola
(74) *Attorney, Agent, or Firm* — Sughrue Mion, PLLC

(57) ABSTRACT

There is provided a gas sensor element for detecting the concentration of a specific gas component in gas under measurement, which includes a plate-shaped element body and a porous protection layer. The element body has, at one end portion thereof, a gas sensing portion formed with a solid electrolyte substrate and a pair of electrodes. The porous protection layer has a porous structure formed of ceramic particles and surrounds at least the circumference of the one end portion of the element body. In the present invention, the porous protection layer has an inner region, an intermediate region and an outer region laminated together in order of mention from the element body toward the outside. The intermediate region has a porosity lower than those of the inner and outer regions. There is also provided a gas sensor with such a gas sensor element.

7 Claims, 5 Drawing Sheets

200 μm

(56) References Cited

OTHER PUBLICATIONS

EPO machine-generated English language translation of CN1329247 A. The translation was made Nov. 19, 2014.*

Communication dated Jul. 31, 2014 from the State Intellectual Property Office of P.R. China in counterpart Chinese Patent Application No. 201210042762.9.

* cited by examiner

100 μm

GAS SENSOR ELEMENT AND GAS SENSOR

BACKGROUND OF THE INVENTION

The present invention relates to a gas sensor element for detecting the concentration of a specific gas component in gas under measurement such as combustion gas or exhaust gas of an internal combustion engine or a combustor etc. and to a gas sensor using the gas sensor element.

Hereinafter, the terms "front" and "rear" are used with respect to the axial direction of a gas sensor (gas sensor element) for purposes of description. These terms are illustrative and are not intended to limit the scope of the present invention.

There has been used a gas sensor having a gas sensor element for detecting the concentration of a specific gas component such as oxygen in exhaust gas of an internal combustion engine. The gas sensor element includes a plate-shaped element body having, at a front end portion thereof, a gas sensing portion provided with a solid electrolyte substrate and a pair of electrodes. When the front end portion of the gas sensor element in which the gas sensing portion of the element body is located (also referred to as "the sensing end portion of the gas sensor element") is exposed to the exhaust gas, poisoning substances such as silicon and phosphorus in the exhaust gas may be adhered to the sensing end portion of the gas sensor element. Water content such as condensed water in the exhaust gas or in an exhaust pipe of the internal combustion engine may also be adhered to the sensing end portion of the gas sensor element. At least the sensing end portion of the gas sensor element is thus covered with a porous ceramic protection layer so as to trap poisoning substances and prevent direct contact of water content with the sensing end portion of the gas sensor element. Japanese Laid-Open Patent Publication No. 2003-322632 discloses one such type of porous protection layer having a two-layer structure in which an inner (lower) layer is higher in porosity than an outer (upper) layer. In this protection layer, the inner layer has roughness due to its high porosity and thereby exhibits anchoring effect so as to improve the adhesion of the inner layer to the outer layer. The inner layer also exhibits thermal insulation effects due its high porosity so as to, even when the gas sensor element gets wet with water (water drop becomes adhered to the porous protection layer), prevent heat from being taken away from the gas sensing portion to the outer layer.

SUMMARY OF THE INVENTION

However, the above-disclosed porous protection layer does not attain a sufficient strength of adhesion between the inner and outer layers just by setting the porosity of the inner layer higher than that of the outer layer. The inner and outer layers of the porous protection layer may be separated when the porous protection layer gets wet with water. In general, the likelihood of separation of the inner and outer layers of the porous protection layer increases with the thickness of the porous protection layer. Further, the above-disclosed porous protection layer does not exert sufficient thermal insulation effect so that heat may be taken away from the gas sensing portion when the gas sensor element gets wet with water.

It is therefore an object of the present invention to provide a gas sensor element having a multilayer porous protection layer capable of enhancing an interlaminar adhesion strength while maintaining thermal insulation effect. It is also an object of the present invention to provide a gas sensor using the gas sensor element.

According to one aspect of the present invention, there is provided a gas sensor element for detecting the concentration of a specific gas component in gas under measurement, comprising: a plate-shaped element body having, at one end portion thereof, a gas sensing portion, the gas sensing portion including a solid electrolyte substrate and a pair of electrodes arranged on the solid electrolyte substrate; and a porous protection layer formed of ceramic particles and surrounding at least the circumference of the one end portion of the element body, wherein the porous protection layer has an inner region, an intermediate region and an outer region laminated together in order of mention from the element body toward the outside; and wherein the intermediate region has a porosity lower than those of the inner and outer regions.

In the gas sensor element, the element body may have a heating unit (heater) capable of generating heat upon energization thereof in addition to the element unit; and the porous protection layer may have, in addition to the above-mentioned inner, intermediate and outer regions, any additional region or regions located outside the outer region.

It is preferable that the porosity of the outer region is lower than that of the inner region. It is also preferable that: the outer region contains, as the ceramic particles, rough particles and fine particles smaller in size than the rough particles; the intermediate region contains the same fine particles as those contained in the outer region; and the proportion of the fine particles in the intermediate region is higher than the proportion of the fine particles in the outer region. It is further preferable that the intermediate region contains the same particles as those contained in the inner region. Furthermore, it is preferable that the intermediate region has a thickness smaller than those of the inner and outer regions.

According to another aspect of the present invention, there is provided a gas sensor comprising: the above gas sensor element; and a housing retaining therein the gas sensor element.

The other objects and features of the present invention will also become understood from the following description.

DESCRIPTION OF THE EMBODIMENTS

The present invention will be described in detail below.

Figure 1:
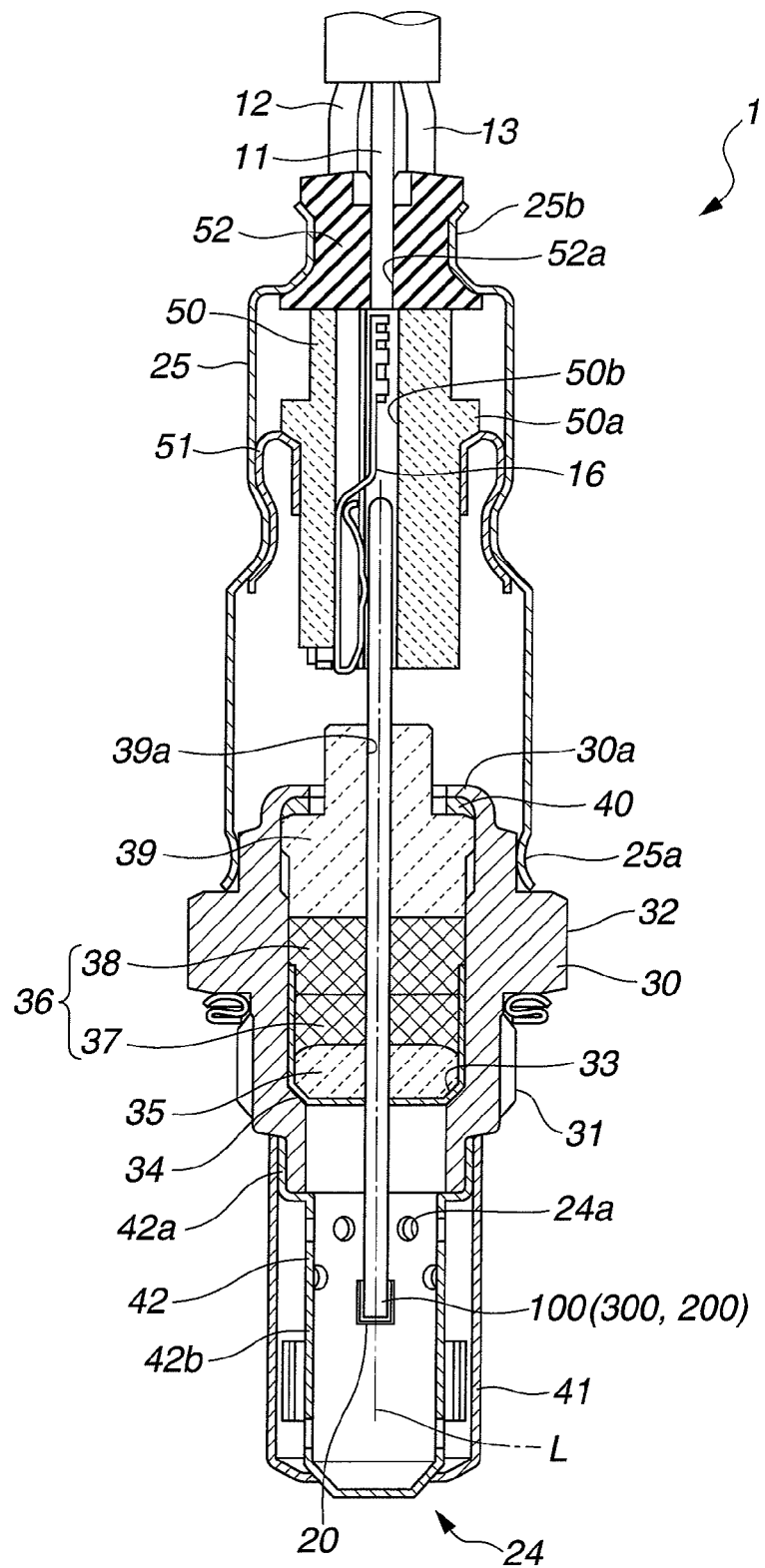
FIG. 1 is a section view of a gas sensor with a gas sensor element according to one embodiment of the present invention.

As shown in FIG. 1, a gas sensor 1 according to one exemplary embodiment of the present invention includes a plate-shaped gas sensor element 100 and a metal shell 30 (as a housing). By way of example, the gas sensor 1 is in the form of an oxygen sensor for detecting the concentration of oxygen in exhaust gas (gas under measurement) flowing through e.g. an exhaust pipe of an internal combustion engine in the present embodiment.

Figure 2:
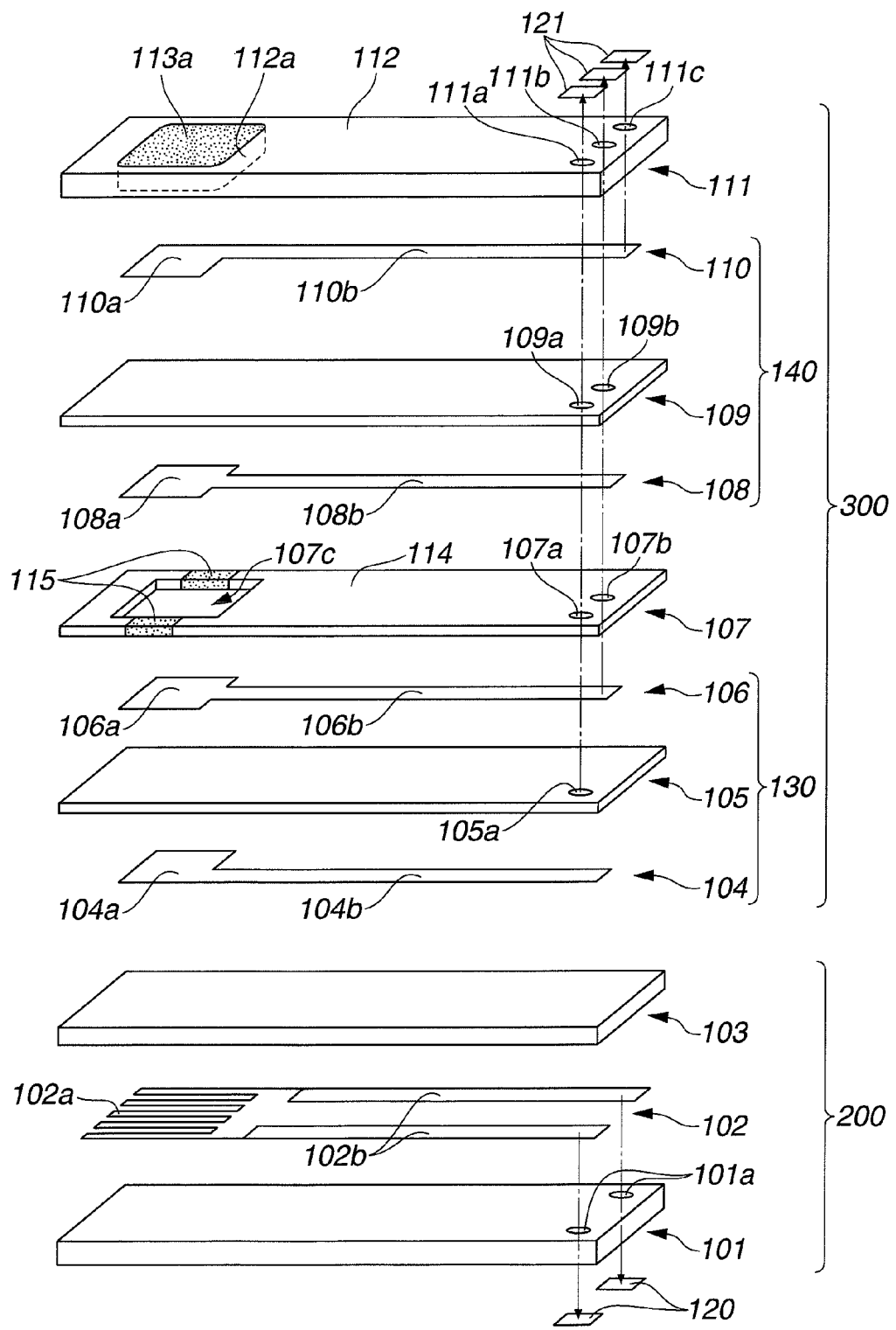
FIG. 2 is an exploded perspective view of the gas sensor element according to the one embodiment of the present invention.

The gas sensor element 100 extends in an axial direction L of the gas sensor 1 and has a plate-shaped element body in which a sensing unit 300 and a heating unit (heater) 200 are laminated together as shown in FIGS. 1 and 2.

The heating unit 200 includes first and second substrates 101 and 103, a heating member 102 and terminal pads (also referred to as "heating-unit-side terminal pads") 120. The first and second substrates 101 and 103 are arranged in such a manner that a longitudinal direction of the substrate 101, 103 is in agreement with the axial direction L of the gas sensor 1. The heating member 102 is arranged between the first and second substrates 101 and 103 and adapted to generate heat upon energization thereof.

As shown in FIG. 2, the heating member 102 has a heating portion 102*a* located at a front end side thereof and a pair of lead portions 102*b* extending from the heating portion 102*a* along the longitudinal direction of the first substrate 101. The heating-unit-side terminal pads 120 are arranged on a main surface of the first substrate 101 opposite from the heating member 102.

Through hole conductors 101*a* are formed through the first substrate 101 so as to electrically connect ends of the lead portions 102*b* to the heating-unit-side terminal pads 120 via the respective through hole conductors 101*a*.

In the heating unit 200, each of the first and second substrates 101 and 103 is formed predominantly of insulating ceramic material such as alumina; and the heating member 102 is formed of predominantly of platinum-group metal. Specific examples of the platinum-group metal are Pt, Rh and Pd. These platinum-group metals can be used solely or in combination of two or more thereof. In view of the heat resistance and oxidation resistance, it is preferable that the heating member 102 is formed predominantly of Pt. It is also preferable that the heating member 102 contains a ceramic component, more preferably the same ceramic component as the main component of the substrate 101, 103, in view of the adhesion of the heating member 102 to the substrate 101, 103.

The sensing unit 300 includes an oxygen concentration detection cell 130 and an oxygen pumping cell 140 laminated to each other.

The oxygen concentration detection cell 130 has a first solid electrolyte substrate 105 arranged in such a manner that a longitudinal direction of the first solid electrolyte substrate 105 is in agreement with the axial direction L of the gas sensor 1 and first and second electrodes 104 and 106 arranged on opposite main surfaces of the first solid electrolyte substrate 105. The first electrode 104 has a first electrode portion 104*a* and a first lead portion 104*b* extending from the first electrode portion 104*a* along the longitudinal direction of the first solid electrolyte substrate 105, whereas the second electrode 106 has a second electrode portion 106*a* and a second lead portion 106*b* extending from the second electrode portion 106*a* along the longitudinal direction of the first solid electrolyte substrate 105.

The oxygen pumping cell 140 has a second solid electrolyte substrate 109 arranged in such a manner that a longitudinal direction of the second solid electrolyte substrate 109 is in agreement with the axial direction L of the gas sensor 1 and third and fourth electrodes 108 and 110 arranged on opposite main surfaces of the second solid electrolyte substrate 109. The third electrode 108 has a third electrode portion 108*a* and a third lead portion 108*a* extending from the third electrode portion 108*b* along the longitudinal direction of the second solid electrolyte substrate 109, whereas the fourth electrode 110 has a fourth electrode portion 110*a* and a fourth lead portion 110*a* extending from the fourth electrode portion 110*a* along the longitudinal direction of the second solid electrolyte substrate 109.

The sensing unit 300 also includes an insulating layer 107 arranged between the oxygen concentration detection cell 130 and the oxygen pumping cell 140, a protection layer 111 arranged on the main surface of the second solid electrolyte substrate 109 opposite from the oxygen concentration detection cell 130 and terminal pads (also referred to as "sensing-unit-side terminal pads") 121 arranged on a surface of the protection layer 111 opposite from the oxygen pumping cell 140.

A first through hole conductor 105*a*, a second through hole conductor 107*a*, a fourth through hole conductor 109*a* and a sixth through hole conductor 111*a* are formed through the first solid electrolyte substrate 105, the insulating layer 107, the second solid electrolyte substrate 109 and the protection layer 111, respectively, so as to electrically connect an end of the first lead portion 104*b* to one of the sensing-unit-side terminal pads 121 via the through hole conductors 105*a*, 107*a*, 109*b* and 111*a*. A third through hole conductor 107*b*, a fifth through hole conductor 109*b* and a seventh through hole conductor 111*b* are formed through the insulating layer 107, the second solid electrolyte substrate 109 and the protection layer 111, respectively, so as to electrically connect an end of the second lead portion 106*b* to another one of the sensing-unit-side terminal pads 121 via the through hole conductors 107*b*, 109*b* and 111*b* and to electrically connect an end of the third lead portion 108*b* to the another one of the sensing-unit-side terminal pads 121 via the though hole conductors 109*b* and 111*b*. The second lead portion 106*b* and the third lead portion 108*b* are herein kept at the same potential. Further, a eighth through hole conductor 111*c* is formed through the protection layer 111 so as to electrically connect an end of the fourth lead portion 110*b* to the remaining one of the sensing-unit-side terminal pads 121 via the through hole conductor 111*c*.

In the sensing unit 300, the first and second solid electrolyte substrates 105 and 109 are formed of partially stabilized zirconia containing yttria ($Y_2O_3$) or calcia (CaO) as a stabilizer; and the first to fourth electrodes 104, 106, 108 and 110, the terminal pads 120 and 121 (also generically called "conducting members") are formed of platinum-group metal. Specific examples of the platinum-group metal are Pt, Rh and Pd. These platinum-group metals can be used solely or in combination of two or more thereof. In view of the heat resistance and oxidation resistance, it is preferable that the conducting members 104, 106, 108, 110, 120 and 121 are formed predominantly of Pt. It is also preferable that each of the conducting members 104, 106, 108, 110, 120 and 121 contains a ceramic component in addition to the platinum-group metal. In this case, the ceramic component of the conducting member 104, 106, 108, 110, 120, 121 is preferably the same as (similar to) that of the adjacent structural part to which the conducting member 104, 106, 108, 110, 120, 121 is laminated (e.g. the main component of the solid electrolyte substrate 105, 109) in view of the adhesion of the conducting member 104, 106, 108, 110, 120, 121 to the adjacent structural part.

The insulating layer 107 has an insulating portion 114 and diffusion limiting portions 115. As shown in FIG. 2, a hollow gas detection chamber 107*c* is defined in the insulating portion 114 of the insulating layer 107 at a position corresponding to the second and third electrode portions 106*a* and 108*a*. The diffusion limiting portions 115 are located on both sides of the gas detection chamber 107*c* in a width direction of the insulating layer 107 so as to provide therethrough gas communication between the gas detection chamber 107c and the outside and allow diffusion of the exhaust gas from the outside into the gas detection chamber 107c under predetermined rate-limiting conditions.

There is no particular limitation on the material of the insulating portion 114 as long as the insulating portion 114 is in the form of an insulating ceramic sintered body. The insulating portion 114 is formed of, for example, oxide ceramic material such as alumina or mullite. On the other hand, the diffusion limiting portions 115 are formed of, for example, porous alumina so as to limit the rate of diffusion of the exhaust gas.

The protection layer 111 is formed on the main surface of the second solid electrolyte substrate 109 so as to sandwich the fourth electrode 110 between the protection layer 111 and the solid electrolyte substrate 109. The protection layer 111 has a porous electrode protecting portion 113a covering the fourth electrode portion 110a and thereby protecting the fourth electrode 104 from poisoning and a reinforcing portion 112 covering the fourth lead portion 110b and protecting the solid electrolyte substrate 109.

Herein, the oxygen concentration detection cell 130 (first solid electrolyte substrate 105 and first and second electrodes 104 and 106) and the gas detection chamber 107c constitutes a gas sensing portion at a front end portion of the sensing unit 300 (i.e. at a front end portion of the element body of the gas sensor element 100) in the present embodiment.

The gas sensor element 100 is configured to adjust the direction and intensity of electric current flowing between the electrodes 108 and 110 of the oxygen pumping cell 140 in such a manner as to control the voltage (electromotive force) between the electrodes 104 and 106 of the oxygen concentration detection cell 130 to a given value (e.g. 450 mV) and determine the concentration of oxygen in the exhaust gas linearly with the electric current flowing through the oxygen pumping cell 140.

The metal shell 30 is formed of, for example, SUS430 and adapted to retain therein the gas sensor element 100, with the front and rear end portions of the element body of the gas sensor element 100 protruding from the metal shell 30. The metal shell 30 has a male thread portion 31 for mounting the gas sensor 1 to the exhaust pipe of the engine and a hexagonal portion 32 for engagement with a mounting tool at the time of mounting. The metal shell 30 also has, at an inner surface thereof, a stepped portion 33 protruding radially inwardly.

A metallic holder 34 is retained in the metal shell 30 by the stepped portion 33 so as to hold therein the gas sensor element 100.

A ceramic holder 35 and a sealing member 36 are arranged in the metallic holder 34, in order of mention from the front side, so as to surround the gas sensor element 100. The sealing member 36 includes a first talc material 37 located on a front side thereof and a second talc material 38 located on a rear side thereof and extending over a rear end of the metallic holder 34. The first talc material 37 is compressed into the metallic holder 34 so as to fix the gas sensor element 100 in the metallic holder 34. The second talc material 38 is compressed into the metal shell 30 so as to establish sealing between the outer surface of the gas sensor element 100 and the inner surface of the metal shell 30.

A sleeve 39 of e.g. alumina is arranged on a rear side of the sealing member 36 so as to surround the gas sensor element 100. The sleeve 39 has a cylindrical shape including a plurality of stepped portions formed on a radially outer surface thereof and an axial hole 39a formed therethrough in the axial direction L so that the gas sensor element 100 passes through the axial hole 39a.

A ring member 40 of e.g. stainless steel is placed on the stepped portion of the sleeve 39. A rear end 30a of the metal shell 30 is bent and crimped radially inwardly so as to push the sleeve 39 via the ring member 40 toward the front of the metal shell 30.

The protector 24 is formed with a plurality of gas holes 24a and welded to the outer circumference of a front end portion of the metal shell 30 so as to cover therewith the protruding front end portion of the gas sensor element 100. The protector 24 has a double structure consisting of a bottomed cylindrical outer protector member 41 having a constant outer diameter and a bottomed cylindrical inner protector member 42 located in the outer protector member 41 and having a rear end portion 42a and a front end portion 42b smaller in outer diameter than the rear end portion 42a.

An outer tube 25 of e.g. SUS 430 is formed with an enlarged-diameter front end portion 25a. This front end portion 25a is fitted on and joined by laser welding etc. to a rear end portion of the metal shell 30 so as to cover therewith the protruding rear end portion of the gas sensor element 100.

A separator 50 is arranged within a rear end portion of the outer tube 25 and has a protruding portion 50a formed on a radially outer surface thereof and an insertion hole 50b formed therethrough in the axial direction. Connection terminals 16 are provided in the insertion hole 50b and connected to the terminal pads 120 and 121 of the gas sensor element 100.

A retaining member 51 is fixed in a gap between the separator 50 and the outer tube 25 by crimping the outer tube 25 radially inwardly with the retaining member 51 engaged with the protruding portion 50a of the separator 50.

Lead wires 11 to 15 are inserted through the insertion hole 50b of the separator 50 and has front ends connected to the connection terminals 16 and rear ends connected to an external control device such as ECU via connectors for electrical connection (signal transmission) between the gas sensor element 100 (sensing unit 300 and heating 200) and the external control device. It is noted that, for purposes of clarity, the wires 14 and 15 are not indicated in the drawings. Each of the lead wires 11 to 15 has a lead line covered with an insulating resin coating although not shown in detail.

A substantially cylidrical rubber cap 52 is fixed in a rear open end of the outer tube 25 by crimping the outer tube 25 radially inwardly with the rubber cap 52 inserted in the rear end of the outer tube 25, so that the rear end of the outer tube 25 is closed with the rubber cap 52.

Figure 3:
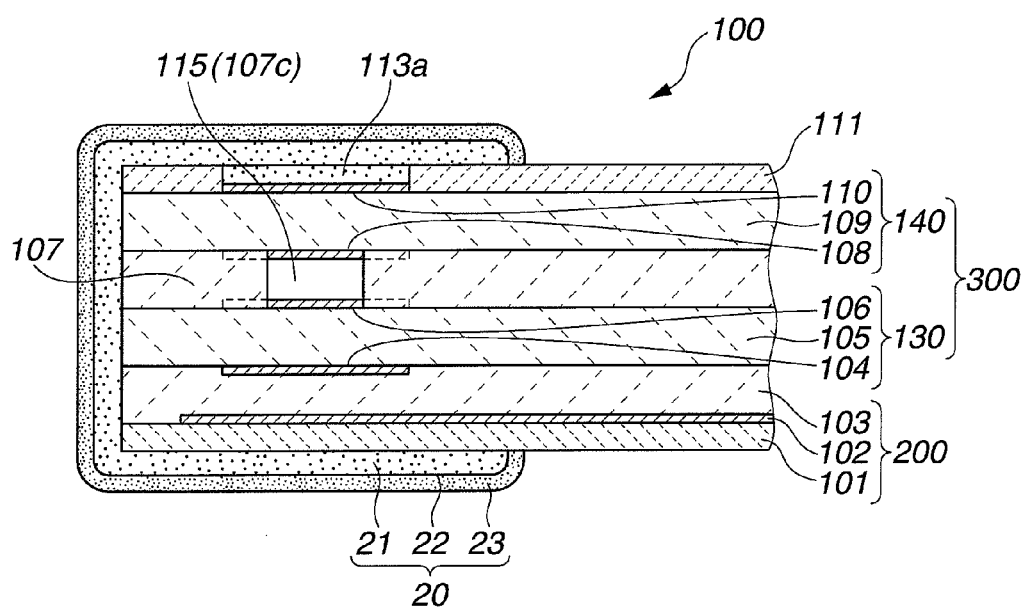
FIG. 3 is an enlarged view of part of the gas sensor element according to the one embodiment of the present invention.

In the present embodiment, the gas sensor element 100 characteristically has a porous protection layer 20 surrounding the entire circumference of the front end portion of the element body as shown in FIGS. 1 and 3. More specifically, the protection layer 20 is formed so as to extend in the axial direction L from a front end face of the sensor element body at least to a point rear of the area where the first to fourth electrode portions 104a, 106a, 108a and 110a overlaps and thereby totally cover not only the front end face but also four lateral sides of the front end portion of the sensor element body as shown in FIG. 3 in the present embodiment.

Figure 4:
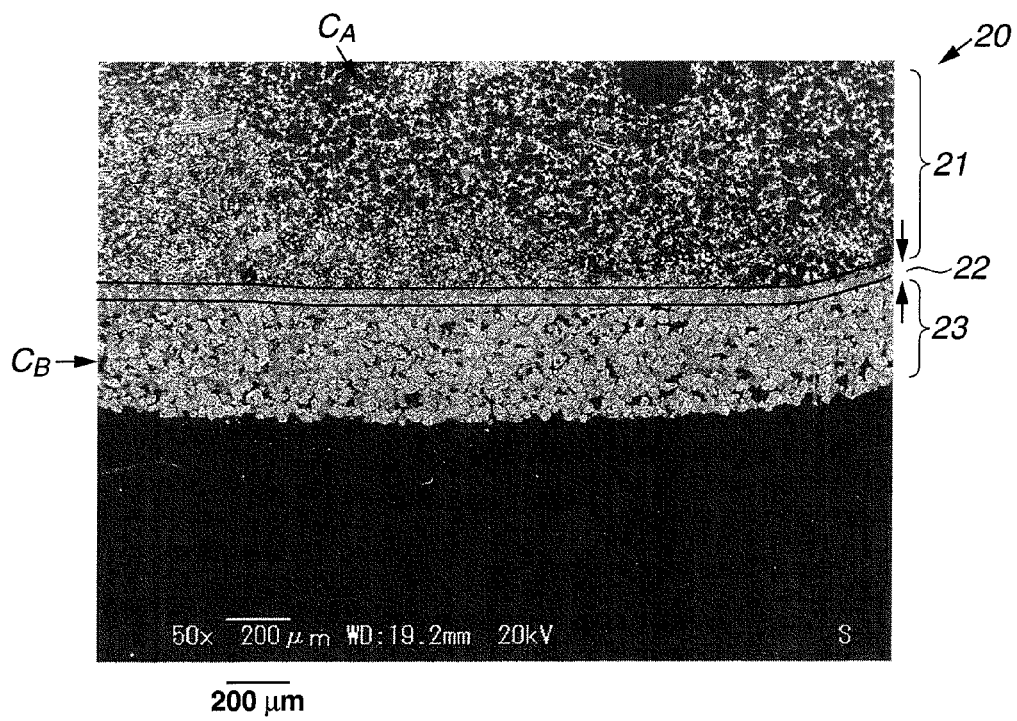
FIG. 4 is an electron micrograph showing a cross section of one example of porous protection layer of the gas sensor element according to the one embodiment of the present invention.
Figure 5:
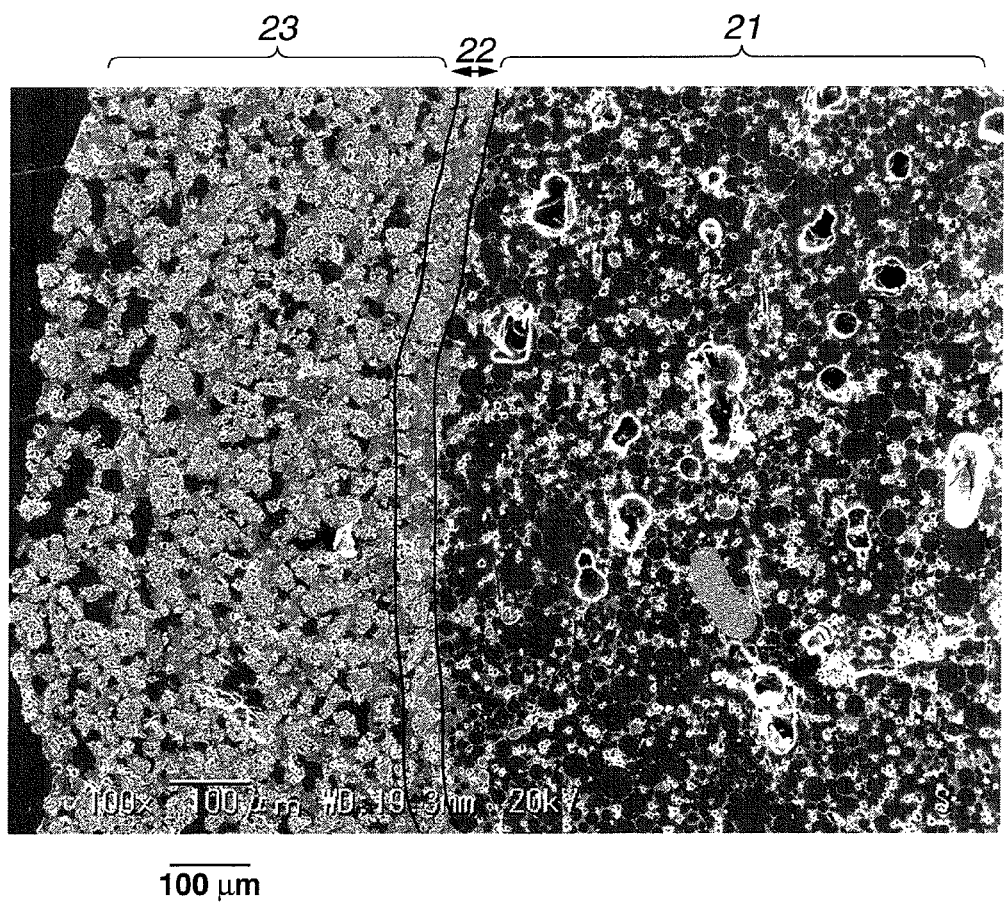
FIG. 5 is an electron micrograph showing a cross section of another example of porous protection layer of the gas sensor element according to the one embodiment of the present invention.

As shown in FIGS. 3 to 5, the porous protection layer 20 has a three-dimensional network structure formed of ceramic particles so as to define a plurality of pores for gas diffusion and includes an inner region 21 located directly on an outer surface of the sensor element body, an outer region 23 located so as to cover an outer surface of the inner region 21 and an intermediate region 22 located between the inner region 21 and the outer region 23. It is noted that, as the intermediate region 22 is much smaller in thickness than the inner and outer regions 21 and 23, the intermediate region 22 is indicated by a line in FIG. 3.

In the present embodiment, the porosity of the intermediate region 22 is set lower than those of the inner and outer layers 21 and 23. That is, the ceramic particles of the intermediate region 22 are more closely packed than those of the inner and outer regions 21 and 23 so as to increase the number of ceramic particles linking the intermediate region 22 to the inner and outer regions 21 and 23. The intermediate region 22 can be thus secured firmly to the inner and outer regions 21 and 23. It is accordingly possible to improve the strength of interlaminar adhesion between the inner region 21 and the intermediate region 22 and between the intermediate region 22 and the outer region 23 of the porous protection layer 20.

As the porosity of the inner region 21 is set higher than that of the intermediate region 22 so that the high-porosity inner region 21 is shielded with the low-porosity intermediate region 22, the thermal insulation effect of the inner region 21 can be increased to, even when the outer region 23 gets wet with water, prevent heat from being taken away from the sensing unit 300 (gas sensing portion) to the outer region 23.

In addition, it is easier to introduce the exhaust gas (gas under measurement) through the pores of the outer region 23 and is possible to secure the gas permeability of the porous protection layer 20 as the porosity of the outer region 23 is set higher than that of the intermediate region 22. It is also possible to trap poisoning substances in the outer region 23 assuredly while allowing assured penetration of condensed water (water drops) into the outer region 23 as the poisoning substances and condensed water are difficult to pass through the intermediate region 21.

The inner region 21, the intermediate region 22 and the outer region 23 are herein defined by the following procedure. In the porous protection layer 20, the area where the ceramic particles change in material, size, shape etc. is determined as a boundary line of the inner region 21 and the intermediate region 22. The area between where the relatively coarse pores are present and where the relatively coarse pores are not present is then determined as a boundary line of the intermediate region 22 and the outer region 23 in parallel with the boundary line of the inner region 21 and the intermediate region 22.

Further, the porosity of the inner region 21, the intermediate region 22 and the outer region 23 are determined by the following image analysis process. A cross-sectional micrograph (SEM image) of the porous protection layer 20 is taken as shown in FIGS. 4 and 5. The thus-obtained image is subjected to binarization in a width direction of each of the inner region 21, the intermediate region 22 and the outer region 23 by commercially available image analysis software, thereby determining the proportion of black area (as indicated by arrows $C_A$ and $C_B$ in FIG. 4) in the image. In the image, the black area corresponds to the pores; and the white area corresponds to the ceramic particles. It means that, the larger the black area, the higher the porosity. In the case where the image analysis area is larger than the thickness of the intermediate region 22, it is feasible to set the image analysis area in such a manner that the whole of the thickness of the intermediate region 22 and determine the porosity of the intermediate region 22 based only on the corresponding black area of the image analysis area.

The inner region 21 is formed by, for example, combining particles of at least one kind of ceramic material selected from the group consisting of alumina, spinel, zirconia, mullite, zircon and cordierite by sintering etc. It is feasible to prepare and sinter a slurry or paste of the ceramic particles and thereby form pores between the ceramic particles of the inner region 21. A combustible pore forming material is preferably added to the slurry or paste so that, when the pore forming material is burned out during the sintering, the spaces filled with the pore forming material remains hollow as pores. The inner region 21 can be thus formed with a low density (high porosity). Examples of the pore forming material are carbon particles, resin beads and organic and inorganic binder particles. Preferably, the inner region 21 has a porosity of 35 to 70% as determined by the above image analysis process in order to secure good thermal insulation effect. If the porosity of the inner region 21 is less than 35%, the total pore volume of the inner region 21 is small so that the thermal insulation effect of the inner region 21 is decreased. If the porosity of the inner region 21 exceeds 70%, it is difficult to maintain the structure of the inner region 21. Further, the thickness of the inner region 21 is preferably in the range of 100 to 800 µm.

The outer region 23 is also formed by, for example, by combining particles of at least one kind of ceramic material selected from the group consisting of alumina, spinel, zirconia, mullite, zircon and cordierite by sintering etc. It is feasible to sinter a slurry or paste containing the ceramic particles and organic or inorganic binder particles so as to burn out the binder particles during the sintering and thereby form pores between the ceramic particles of the outer region 23. As the ceramic particles, rough particles and fine particles smaller in size than the rough particles are preferably used in combination. By the use of such ceramic particles, the outer region 23 can be structured to trap a larger amount of poisoning substances and keep a larger amount of water content penetrating therein. The strength of adhesion between the outer region 23 and the intermediate region 22 can also be improved as the fine particles migrate from the outer region 23 toward the inner region 21 to constitute the intermediate region 22 during the sintering as will be explained later in detail. Preferably, the outer region 23 has a porosity of 10 to 50% as determined by the above image analysis process in order to secure sufficient poisoning substance trapping/water penetrating effect without causing deterioration in gas permeability. If the porosity of the outer region 23 is less than 10%, it is likely that the outer region 23 will be clogged with the poisoning substances. If the porosity of the outer region 23 exceeds 50%, the water may penetrate into the inside of the outer region 23 so as to thereby cause deterioration in water resistance. Further, the thickness of the outer region 23 is preferably in the range of 100 to 800 µm.

There is no particular limitation on the relationship between the porosity of the inner region 21 and the porosity of the outer region 23. Although the porosity of the inner region 21 can be the same as the porosity of the outer region 23, it is preferable that the porosity of the outer region 23 is lower than the porosity of the inner region 21 so as to effectively trap the poisoning substances in the outer region 23 and keep water penetrating in the outer region 23.

Preferably, the intermediate region 21 contains the same ceramic particles as those contained in the inner region 21 and contains the same fine ceramic particles as those contained in the outer region 23. When the intermediate region 22 contains the same ceramic particles as those contained in the inner region 21, it is possible to improve the adhesion of the intermediate region 22 to the inner region 21. It is also possible to improve the adhesion of the intermediate region 22 to the outer region 23 when the intermediate region 22 also contains the same fine ceramic particles as those contained in the outer region 23. In particular, the proportion of the fine ceramic particles in the intermediate region 22 is preferably set higher than the proportion of the fine ceramic particles in the outer region 23 so as to control the porosity of the intermediate region 22 to be lower than those of the inner and outer regions 21 and 23. It is noted that: the proportion of the fine ceramic particles in the intermediate region 22 refers to the ratio of the content of the fine ceramic particles in the intermediate region 22 to the total content of the ceramic particles in the intermediate region 22; and the proportion of the fine ceramic particles in the outer region 23 refers to the ratio of the content of the fine ceramic particles in the outer region 23 to the total content of the ceramic particles (rough and fine ceramic particles) in the outer region 23. The content of the fine particles in each of the intermediate region 22 and the outer region 23 can be determined from the amount of the fine particles per unit area in the intermediate region 22 or outer region 23 based on the cross-sectional micrograph (SEM image).

The thickness of the intermediate region 22 is preferably smaller than those of the inner and outer regions 21 and 23 as mentioned above in the present embodiment. It is possible by such thickness control to more properly secure the thermal insulation effect of the inner region 21 and the poisoning substance trapping/water penetrating effect of the outer region 23 in the porous protection layer 20 while improving the strength of adhesion between the inner and outer regions 21 and 23 by the intermediate region 22. More specifically, the thickness of the intermediate region 22 is preferably in the range of 20 to 80 μm.

For example, the above-mentioned porous protection layer 20 can be formed by the following procedure.

Figure 6A:
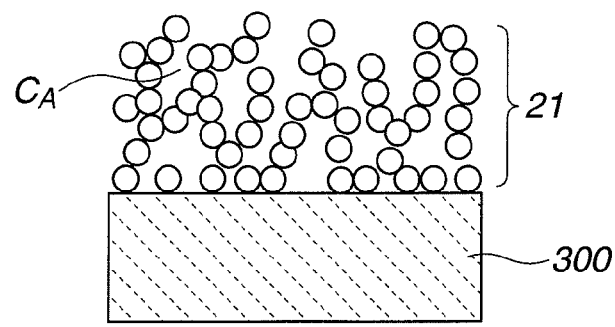
FIGS. 6A, 6B and 6C are schematic views showing one example of process for forming the porous protection layer.

A slurry for formation of the inner region 21 (referred to as "inner-region slurry") and a slurry 23x for formation of the outer region 23 (referred to as "outer-region slurry") are first prepared. As mentioned above, a combustible pore forming material is added to the inner-region slurry; and rough ceramic particles 231 and fine ceramic particles 232 smaller in size than the rough ceramic particles 231 are used in the outer-region slurry 23x The inner-region slurry is applied by dipping etc. to the entire circumference of the front end portion of the sensor element body and sintered. As shown in FIG. 6A, the pore forming material is burned out during the sintering to thereby define relatively large pores $C_A$ between the ceramic particles.

Figure 6B:
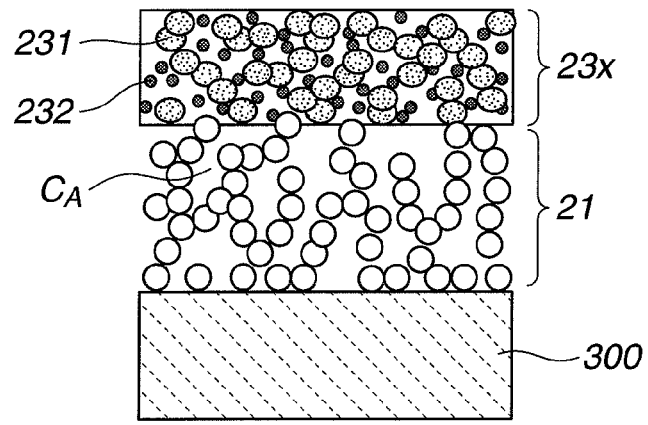

The outer-region slurry 23x is next applied by dipping etc. to the above-formed inner coating. When the outer-region slurry 23x is applied to the inner coating, some of the fine particles 232 contained in the outer-region slurry 23x become embedded into the pores $C_A$ of the boundary surface of the inner coating as shown in FIG. 6B. In this state, the outer-region slurry 23x is sintered.

Figure 6C:
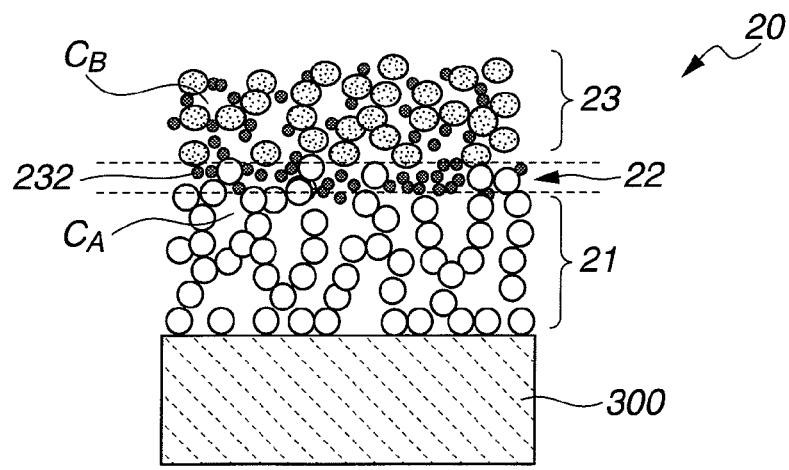

During the sintering, the region of the resulting laminated coating where the some of the fine ceramic particles 232 are embedded in the pores $C_A$ of the surface of the inner coating becomes the intermediate region 22 as shown in FIG. 6C. The intermediate region 22 can be thus easily formed. Then, the region of the laminated coating located inside the intermediate region 22 becomes the inner region 21; and the region of the laminated coating located outside the intermediate region 22 becomes the outer region 23. Even though the amount of the fine particles present in the area of the outer region 23 adjacent to the intermediate region 22 decreases due to the migration of the fine particles, the rough particles remain and constitute a porous body. The outer region 23 can be thus formed stably with a three-dimensional network structure in which pores $C_B$ are defined between the rough and fine particles 231 and 232.

Alternatively, the porous protection layer 20 may be produced by applying and sintering slurries for formation of the inner region 21, the intermediate region 22 and the outer region 23 (referred to as "inner-region slurry", "intermediate-region slurry" and "outer-region slurry") in order. In this case, it is feasible to apply and sinter the inner-region slurry, apply and sinter the intermediate-region slurry, and then, apply and sinter the outer-region slurry, or feasible to apply the inner-region slurry, the intermediate-region slurry and the outer-region slurry successively, and then, sinter the inner-region slurry, the intermediate-region slurry and the outer-region slurry simultaneously. It is needless to say that, in the case of preparing and applying the inner-region slurry, the intermediate-region slurry and the outer-region slurry separately, the outer-region slurry does not necessarily contain both of rough particles and fine particles.

EXAMPLES

Example (Sample Production)

Samples of the plate-shaped gas sensor element 100 shown in FIGS. 1 and 2 were each produced by forming the porous protection layer 20 as follows.

A slurry A was prepared as an inner-region slurry by mixing 40 vol % of alumina powder (particle size distribution: D10=0.24 μm, D50=0.40 μm, D90=0.60 μm), 60 vol % of carbon powder (particle size distribution: D10=10.5 μm, D50=20.6 μm, D90=42.2 μm) and 10 vol % of separately prepared alumina sol with ethanol. The prepared slurry A was adjusted to an appropriate viscosity and applied by dipping (immersion) process to the entire circumference (four sides) of the front end portion of the sensor element body (sensing unit 300 and heating unit 200) in such a manner that the coating of the slurry A was 300 μm in thickness. The applied slurry coating was dried in a dryer at 200° C. for several hours, thereby removing excessive organic solvent from the slurry coating. The dried slurry coating was then sintered in the air at 1100° C. for 3 hours.

Further, a slurry B was prepared as an outer-region slurry by mixing 60 vol % of spinel powder (particle size distribution: D10=24.6 μm, D50=44 μm, D90=88 μm), 40% of alumina powder (particle size distribution: D10=0.24 μm, D50=0.40 μm, D90=0.60 μm) and 10 vol % of separately prepared alumina sol with ethanol. The prepared slurry B was adjusted to an appropriate viscosity and applied by dipping (immersion) process to a surface of the above-formed inner coating in such a manner that the coating of the slurry B was 250 μm in thickness. The applied slurry coating was dried in a dryer at 200° C. for several hours, thereby removing excessive organic solvent from the slurry coating. The dried outer slurry coating was then sintered in the air at 1100° C. for 3 hours.

Herein, the particle size distribution of the powder material used in the slurry A, B refers to the cumulative particle size distribution of the particles as measured by laser diffraction scattering where D10, D50 and D90 are particle sizes at 10%, 50% and 90% cumulation from the fine particle side of the cumulative particle size distribution, respectively.

The thus-obtained gas sensor element 100 with the protection layer 20 was cut in a direction orthogonal to the axial direction L. A cross-sectional micrograph of the porous protection layer 20 was then taken by a scanning electron microscope (SEM). The inner region 21, the intermediate region 22 and the outer region 23 were determined based on the cross-sectional SEM image. Further, each of the porosity of the inner region 21, the porosity of the intermediate region 22 and the porosity of the outer region 23 was determined based on the cross-sectional SEM image by the above-mentioned image analysis process. The image analysis area was herein 100 μm×100 μm in each image analysis process.

(Evaluation Test)

The following water resistance test was performed on the produced samples of the gas sensor element 100.

The gas sensor element 100 was set to 800° C. in the air. In this state, twenty water drops of 3 μl, or 10 μL were successively dropped from above onto a position of the porous protection layer 20 corresponding to the gas diffusion hole (diffusion limiting portion 115). After the dropping, the appearance of the porous protection layer 20 was observed with a magnifying glass to visually check the occurrence of damage to the porous protection layer 20 (e.g. separation of the porous protection layer 20, crack in the porous protection layer 20 etc.). Then, the porous protection layer 20 was peeled off from the element body of the gas sensor element 100. The occurrence of crack in the element body of the gas sensor element 100 was visually checked by so-called "red check". In Table 1, the test results are indicated in terms of the number of the samples in which the damage occurred to the porous protection layer 20 and the number of the samples in which the crack occurred in the element body of the gas sensor element 100.

Comparative Example

Samples of gas sensor element were produced in the same manner as in Example, except for using a slurry C in place of the slurry B for formation of the porous protection layer. The slurry C was herein prepared by mixing spinel powder (particle size distribution: D10=24.6 μm, D50=44 μm, D90=88 μm) and 10 vol % separately prepared alumina sol with ethanol.

The thus-obtained gas sensor element was subjected to SEM image analysis in the same manner as in Example. It was confirmed by the image analysis that: the porous protection layer consisted of inner and outer layers. There was seen no intermediate region lower in porosity than the inner and outer layers. The reason for the formation of no intermediate region is assumed that the fine alumina particles were contained in the slurry B but were not contained in the slurry C so that, when the slurry C was applied to the inner coating, some of the fine alumina particles did not become embedded and filled in pores of the inner coating.

Further, the produced samples of the gas sensor element were subjected to water resistance test in the same manner as in Example.

The test results are indicated in TABLE 1.

water drop volume of the water resistance test in Example. The gas sensor element 100 of Example had high water resistance.

In Comparative Example, by contrast, more than half of the samples had damage to the porous protection layer and crack in the sensor element body in the case where the water drop volume of the water resistance test was 3 μL; and all of the samples had damage to the porous protection layer and crack in the sensor element body in the case where the water drop volume of the water resistance test was 10 μL. The gas sensor element of Comparative Example was inferior in water resistance. It is assumed that, in the absence of the intermediate region in Comparative Example, separation of the inner and outer layers occurred when the porous protection layer was wetted with water.

The entire contents of Japanese Patent Application No. 2011-035583 (filed on Feb. 22, 2011) and No. 2011-276929 (filed on Dec. 19, 2011) are herein incorporated by reference.

Although the above-mentioned embodiment specifically refers to the oxygen sensor (oxygen sensor element), the present invention is not limited to the above-embodied oxygen sensor (oxygen sensor element). The present invention is applicable to various gas sensors (gas sensor elements) in which a sensing unit has a solid electrolyte substrate and a pair of electrodes. Various modifications and variations of the embodiment described above are possible without departing from the scope of the present invention. For example, the gas sensor (gas sensor element) of the present invention can be embodied as not only an oxygen sensor (oxygen sensor element) for detecting the concentration of $O_2$ in gas under measurement but also a NOx sensor (NOx sensor element) for detecting the concentration of NOx in gas under measurement, a HC sensor (HC sensor element) for detecting the concentration of HC in gas sunder measurement and the like. Although the porous protection layer 20 is formed of ceramic particles in the above embodiment, the porous protection layer 20 may be formed by mixing ceramic particles with ceramic fibers.

The scope of the invention is defined with reference to the following claims.

What is claimed is:

1. A gas sensor element for detecting the concentration of a specific gas component in gas under measurement, comprising:
   a plate-shaped element body having, at one end portion thereof, a gas sensing portion, the gas sensing portion including a solid electrolyte substrate and a pair of electrodes arranged on the solid electrolyte substrate; and

TABLE 1

|  | Porosity of porous protection layer | | | Water resistance test (water drop: 3 μL) | | Water resistance test (water drop: 10 μL) | |
| --- | --- | --- | --- | --- | --- | --- | --- |
|  | Inner region layer) | Intermediate region | Outer region (layer) | Damage to protection layer | Crack in sensor element | Damage to protection layer | Crack in sensor element |
| Example | 62% | 23% | 38% | 0 | 0 | 0 | 0 |
| Comparative Example | 62% | — | 40% | 6 | 6 | 10 | 10 |

As shown in TABLE 1, there was no damage to the porous protection layer 20 and no crack in the element body of the gas sensor element 100 in any of the samples regardless of the a gas-permeable porous protection layer formed of ceramic particles and surrounding at least the circumference of the one end portion of the element body, wherein the porous protection layer has an inner region, an intermediate region and an outer region laminated together in order of mention from the element body toward the outside; and wherein the intermediate region has a porosity lower than those of the inner and outer regions.

2. The gas sensor element according to claim 1, wherein the porosity of the outer region is lower than that of the inner region.

3. The gas sensor element according to claim 1, wherein the outer region contains, as the ceramic particles, rough particles and fine particles smaller in size than the rough particles; wherein the intermediate region contains the same fine particles as those contained in the outer region; and wherein the proportion of the fine particles in the intermediate region is higher than the proportion of the fine particles in the outer region.

4. The gas sensor element according to claim 1, wherein the intermediate region contains the same kind of particles as those contained in the inner region.

5. The gas sensor element according to claim 1, wherein the intermediate region has a thickness smaller than those of the inner and outer regions.

6. A gas sensor, comprising:
the gas sensor element according to claim 1; and
a housing retaining therein the gas sensor element.

7. The gas sensor element according to claim 1, wherein the porous protection layer surrounds the entire circumference of the one end portion of the element body.

* * * * *